United States Patent
Campbell et al.

(10) Patent No.: US 8,993,798 B2
(45) Date of Patent: *Mar. 31, 2015

(54) ISOMERIZED ALPHA OLEFIN SULFONATE AND METHOD OF MAKING THE SAME

(75) Inventors: Curtis Bay Campbell, Hercules, CA (US); Andrew J. Howes, Chesterfield, VA (US)

(73) Assignee: Chevron Oronite Company LLC, San Ramon, CA (US)

( * ) Notice: Subject to any disclaimer, the term of this patent is extended or adjusted under 35 U.S.C. 154(b) by 852 days.

This patent is subject to a terminal disclaimer.

(21) Appl. No.: 12/962,818

(22) Filed: Dec. 8, 2010

(65) Prior Publication Data

US 2011/0152571 A1    Jun. 23, 2011

Related U.S. Application Data

(60) Provisional application No. 61/289,091, filed on Dec. 22, 2009.

(51) Int. Cl.
  *C07C 303/06*  (2006.01)
  *C07C 303/26*  (2006.01)
  *C07C 309/20*  (2006.01)

(52) U.S. Cl.
  CPC .................................. *C07C 309/20* (2013.01)
  USPC ................................ 562/30; 562/123; 558/55

(58) Field of Classification Search
  USPC ....................................... 562/30, 123; 558/55
  See application file for complete search history.

(56) References Cited

U.S. PATENT DOCUMENTS

| | | | |
|---|---|---|---|
| 3,332,874 A * | 7/1967 | Coward et al. | 510/429 |
| 3,708,437 A * | 1/1973 | Sweeney | 510/428 |
| 4,061,063 A | 12/1977 | Rubinfeld | |
| 6,043,391 A | 3/2000 | Berger et al. | |
| 6,132,638 A | 10/2000 | Oldenhove | |
| 6,730,750 B2 | 5/2004 | Eaton et al. | |
| 6,911,505 B2 | 6/2005 | Small | |
| 2009/0112014 A1 | 4/2009 | Campbell et al. | |

OTHER PUBLICATIONS

B. Elvers, et al., Ed. Ullmann's Encyclopedia of Industrial Chemistry, vol. A13, VCH Verlagsgesellschaft mbH, Weinheim, 1989, p. 243-247 and 275-276.
B. Cornils, et al., Ed., Applied Homogeneous Catalysis with Organometallic Compounds, A Comprehensive Handbook, vol. 1, VCH Verlagsgesellschaft mbH, Weinheim, 1996, p. 245-258.
Doddrell, D.T.; D. T. Pegg; M.R. Bendall, Journal of Magnetic Resonance 1982, 48, 323ff.
Lindeman, L. P., Journal of Qualitative Analytical Chemistry 43, 1971 1245ff; Netzel, D.A., et.al., Fuel, 60, 1981, 307ff.
Raney, et al. "Use of High-Active Alpha Olefin Sulfonates in Laundry Powders", Journal of Surfactants and Detergents, vol. 1, No. 3, (Jul. 31, 1998), pp. 361-369.

* cited by examiner

*Primary Examiner* — Sikarl Witherspoon

(57) ABSTRACT

The present invention is directed to an isomerized alpha olefin sulfonate and a method of making the same wherein the isomerized alpha olefin sulfonate is derived from sulfonating an isomerized alpha olefin with sulfur trioxide in the presence of air thereby producing an isomerized alpha olefin sulfonic acid, wherein the isomerized alpha olefin is derived from the isomerization of $C_{12}$-$C_{20}$ normal alpha olefins; and neutralizing the isomerized alpha olefin sulfonic acid with a source of an alkali metal or ammonium or substituted ammonium ion.

5 Claims, No Drawings

ISOMERIZED ALPHA OLEFIN SULFONATE AND METHOD OF MAKING THE SAME

PRIORITY

This application claims benefit of U.S. Provisional Application No. 61/289,091 filed Dec. 22, 2009, the contents of which are incorporated herein by reference.

The present invention is directed to an isomerized alpha olefin sulfonate and a method of making the same.

BACKGROUND OF THE INVENTION

Alpha-olefins, especially those containing about 6 to about 20 carbon atoms, are important items of commerce, with about 1.5 million tons reportedly being produced in 1992. Alpha-olefins are also used as intermediates in the manufacture of detergents, as monomers (especially in linear low density polyethylene), and as intermediates for many other types of products. Alpha-olefins may also be employed in the oilfield drilling fluids market. The use of alpha-olefins as such, and alpha-olefins isomerized to internal olefins, has increased in recent years. As a consequence, improved methods of making these compounds are of value.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243-247 and 275-276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245-258. The major types of commercially used catalysts are alkylaluminum compounds, certain nickel-phosphine complexes, and a titanium halide with a Lewis acid such as diethylaluminum chloride (DEAC). In all of these processes significant amounts of vinylidene and/or tri-substituted and/or internal olefins and/or diolefins, can be produced depending on the carbon number of the olefin and the specific process. Since in most instances these are undesired, and often difficult to separate from the desired linear alpha-olefins, minimization of these byproducts is sought. Small, U.S. Pat. No. 6,911,505 discloses processes for the production of alpha-olefins, including dimerization and isomerization of olefins using a cobalt catalyst complex are provided herein. The olefins so produced are described in this patent as being useful as monomers in further polymerization reactions and useful as chemical intermediates.

Eaton, et al., U.S. Pat. No. 6,730,750 is directed to improved drag reducing agents and methods of forming improved drag reducing agents comprising the steps of isomerizing olefin monomers to form isomerized olefin monomers, polymerizing the isomerized olefin monomers in the presence of at least one catalyst to form a polyolefin drag reducing agent having unexpectedly superior drag reduction properties when combined with liquid hydrocarbons, such as viscous crude oil. This patent further discloses that the drag reducing agents may be introduced into conduits, such as pipelines, to increase the flow of the hydrocarbons through the conduit.

SUMMARY OF THE INVENTION

The present invention is directed to an isomerized alpha olefin sulfonate. The present invention is also directed to a method of making the isomerized alpha olefin sulfonate.

In one embodiment, the present invention is directed to an isomerized alpha olefin sulfonate having the general formula:

wherein R is an aliphatic hydrocarbyl group containing one or more olefin or alcohol moieties or mixtures thereof derived from an isomerized alpha olefin having a Branching Index (BI) from about 10 to about 30, a Branching Proximity (BP) from about 5 to about 36 and a Free Carbon Index (FCI) from about 1 to about 10 and having from about 12 to about 20 carbon atoms; and wherein M is a mono-covalent cation.

In one embodiment, the present invention is directed to a method of making an isomerized alpha olefin sulfonate comprising the steps of (a) sulfonating an isomerized alpha olefin with sulfur trioxide in the presence of air thereby producing primarily an isomerized alpha olefin sulfonic acid, wherein the isomerized alpha olefin is derived from the isomerization of $C_{12}$-$C_{20}$ normal alpha olefins and has a Branching Index (BI) from about 10 to about 30, a Branching Proximity (BP) from about 5 to about 36 and a Free Carbon Index (FCI) from about 1 to about 10;

(b) optionally thermally digesting the product from step (a);

(c) neutralizing the product from step (b) with a source of alkali or alkaline earth metal or amines such as ammonia; and (d) optionally, hydrolyzing the product from step (c) with additional base or caustic.

DETAILED DESCRIPTION OF THE INVENTION

Definitions

As used herein, the following terms have the following meanings unless expressly stated to the contrary:

The terms "active" or "actives" as used herein refers to the concentration of the metal salt of the sulfonate as described herein.

The term "isomerized alpha olefin (IAO)" as used herein refers to an alpha olefin that has been subjected to isomerization conditions which result in an alteration of the distribution of the olefin species present and/or the introduction of branching along the alkyl chain. The isomerized olefin product may be obtained by isomerizing a linear alpha olefin containing from about 12 to about 20 carbon atoms, and more preferably from about 12 to about 18 carbon atoms.

The term "alkali metal" as used herein refers to Group IA metals of the Periodic Table.

The term "Branching Index" (BI) is defined as the percent methyl hydrogens among the total aliphatic hydrogens contained in the isomerized alpha olefin.

The term "Branching Proximity" (BP) is defined as the percent epsilon-$CH_2$ carbons among the total carbons contain in the isomerized alpha olefin.

The term "Free Carbon Index" (FCI) is defined as the total number of epsilon-$CH_2$ carbons contained in the isomerized alpha olefin.

The term "epsilon-$CH_2$" carbons is defined as recurring $CH_2$ carbon located 5 or more $CH_2$ carbon atoms away from a branched carbon along the hydrocarbon chain of the isomerized alpha olefin as indicated in the following simple hydrocarbon molecule:

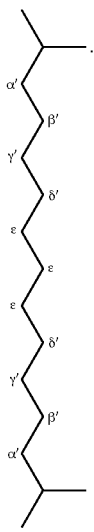

Unless otherwise specified, all percentages are in weight percent and the pressure is atmospheric pressure.

The present invention is directed to an isomerized alpha olefin sulfonate and a method of making the isomerized alpha olefin sulfonate.

The Isomerized Alpha Olefin Sulfonate

The isomerized alpha olefin sulfonate of the present invention has the general formula:

$$R-SO_3M$$

wherein R is an aliphatic hydrocarbyl group containing one or more olefin or alcohol moieties or mixtures thereof derived from an isomerized alpha olefin having from about 12 to about 20 carbon atoms, having a Branching Index of from about 10 to about 30, having a Branching Proximity of from about 5 to about 36 and having a Free Carbon Index of from about 1 to about 10 and; and wherein M is a mono-covalent cation. Preferably, M is an alkali metal or ammonium or substituted ammonium ion. Preferably, the alkali metal is sodium.

Examples of substituted ammonium include ammonium independently substituted with from about 1 to about 4 aliphatic or aromatic hydrocarbyl groups having from about 1 to about 15 carbon atoms, such as alkyl, aryl, alkaryl and aralkyl, and optionally having one or more heteroatoms, such as nitrogen, oxygen or sulfur, which may be present in aliphatic or aromatic heterocyclic rings. Examples of suitable heterocyclic ring substituents include pyrrole, pyrrolidine, pyridine, pyrimidine, pyrazole, imidazole and quinoline. The heterocyclic ring substituent may be substituted on the ammonium moiety through a carbon atom in the heterocyclic ring, such as in a C-pyridyl-substituted ammonium, or, alternatively, the quaternary ammonium nitrogen itself may be a nitrogen atom in the heterocyclic ring, such as in a pyridinium ion.

In one embodiment, the present invention is directed to a sodium isomerized olefin sulfonate (IOS) made by the sulfonation of an isomerized alpha olefin (IAO) in which the IAO is an aliphatic hydrocarbyl group and is made by the isomerization of $C_{10}$-$C_{20}$ normal alpha olefins (NAO), preferably $C_{12}$-$C_{18}$ normal alpha olefins, most preferred $C_{16}$-$C_{18}$ normal alpha olefins. In one embodiment, the sodium isomerized olefin sulfonate (IOS) is made by the sulfonation of an isomerized alpha olefin (IAO) in which the IAO is made by the isomerization of $C_{16}$-$C_{18}$ normal alpha olefins and the IAO has a Branching Index (BI) of about 17, a Branching Proximity (BP) of about 33 and a Free Carbon Index (FCI) of about 7.

In one embodiment, the sodium isomerized olefin sulfonate (IOS) is made by the sulfonation of an isomerized alpha olefin (IAO) in which the IAO is made by the isomerization of $C_{12}$-$C_{14}$ normal alpha olefins and the IAO has a Branching Index (BI) of about 26, a Branching Proximity (BP) of about 9 and a Free Carbon Index (FCI) of about 2.

In one embodiment, the sodium isomerized olefin sulfonate (IOS) is made by the sulfonation of an isomerized alpha olefin (IAO) in which the IAO is made by the isomerization of $C_{16}$-$C_{18}$ normal alpha olefins and the IAO has a Branching Index (BI) of o about 23, a Branching Proximity (BP) of about 13 and a Free Carbon Index (FCI) of about 3.

In one embodiment, the isomerized alpha olefin has an average number of branches per molecule of the isomerized alpha olefin of from about 0.2 to about 0.6.

In one embodiment of the present invention, the normal alpha olefins are isomerized using at least one of a solid or liquid catalyst. The NAO isomerization process can be carried out in either a batch reactor, semi-batch reactor, continuous fixed bed reactor or combination of these reaction processes using homogenous or heterogenous catalysts. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl ($Fe(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at about 150° C. under vacuum or flowing inert, dry gas. After activation, the temperature of the isomerization catalyst is adjusted to the desired reaction temperature and a flow of the olefin is introduced into the reactor. Furthermore, the isomerization process is carried out in a liquid phase (i.e., in the absence of a vapor phase) at atmospheric pressure. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of Branching Index, Branching Proximity and Free Carbon Index.

Sulfonation

Sulfonation of the IAO may be performed by any method known to one of ordinary skill in the art to produce an IAO sulfonic acid intermediate. The sulfonation reaction is typically carried out in a continuous falling film tubular reactor maintained at about 30° C. to about 75° C. The charge mole ratio of sulfur trioxide to olefin is maintained at about 0.3 to 1.1:1.

Other sulfonation reagents, such as sulfuric acid, chlorosulfonic acid or sulfamic acid may also be employed. Preferably, the isomerized alpha olefin is sulfonated with sulfur trioxide diluted with air.

Optionally, the product from the sulfonation process may then be thermally digested by heating.

Neutralization of the Isomerized Alpha Olefin Sulfonic Acid

Neutralization of the IAO sulfonic acid may be carried out in a continuous or batch process by any method known to a person skilled in the art to produce the IOS. Typically, an IAO sulfonic acid is neutralized with a source of a mono-covalent cation. Preferably, the mono-covalet cation is an alkali metal or ammonium or substituted ammonium ion. Preferably, the alkali metal is sodium.

Optionally, the neutralized isomerized alpha olefin sulfonate may be further hydrolyzed with additional base or caustic.

Method of Making an Isomerized Alpha Olefin Sulfonate

A method of making an isomerized alpha olefin sulfonate comprises the steps of (a) sulfonating an isomerized alpha olefin with sulfur trioxide in the presence of air thereby producing primarily an isomerized alpha olefin sulfonic acid, wherein the isomerized alpha olefin is derived from the isomerization of $C_{10}$-$C_{20}$ normal alpha olefins and has a Branching Index (BI) from about 10 to about 30, a Branching Proximity (BP) from about 5 to about 36 and a Free Carbon Index (FCI) from about 1 to about 10; (b) optionally thermally digesting the product from step (a); (c) neutralizing the product from step (b) with a source of an alkali metal or ammonium; and (d) optionally, hydrolyzing the product from step (c) with additional base or caustic.

The isomerized alpha olefin has from about 10 to about 40 carbon atoms, and a Branching Index (BI) from about 10 to about 30, a Branching Proximity (BP) from about 5 to about 36 and a Free Carbon Index (FCI).

The isomerized alpha olefin has from about 10 to about 20 carbon atoms, and a Branching Index (BI) from about 10 to about 30, a Branching Proximity (BP) from about 5 to about 36 and a Free Carbon Index (FCI).

In one embodiment, the sodium isomerized olefin sulfonate (IOS) is made by the sulfonation of an isomerized alpha olefin (IAO) in which the IAO is made by the isomerization of $C_{16}$-$C_{18}$ normal alpha olefins and the IAO is composed of at least about 23% branching. In one embodiment, the sodium isomerized olefin sulfonate (IOS) is made by the sulfonation of an isomerized alpha olefin (IAO) in which the IAO is made by the isomerization of $C_{12}$-$C_{14}$ normal alpha olefins and the IAO is composed of at least about 65% branching. In one embodiment, the sodium isomerized olefin sulfonate (IOS) is made by the sulfonation of an isomerized alpha olefin (IAO) in which the IAO is made by the isomerization of $C_{16}$-$C_{18}$ normal alpha olefins and the IAO is composed of at least about 65% branching.

Other embodiments will be obvious to those skilled in the art.

The following examples are presented to illustrate specific embodiments of this invention and are not to be construed in any way as limiting the scope of the invention.

EXAMPLE 1

Preparation of 65% Branched Isomerized $C_{12}$/$C_{14}$ Alpha Olefin

The primary olefinic species in Normal Alpha Olefins (NAO's) is normally alpha-olefin. The isomerization of NAO's occurs by contacting the NAO's over the solid acid extrudate catalyst ICR 502 (purchased from Chevron Lummnus Global) which isomerizes the alpha-olefin to other olefinic species, such as beta-olefins, internal olefins and even tri-substituted olefins. The isomerization of NAO's over ICR 502 catalyst also induces skeletal isomerization in which methyl groups are introduced along the hydrocarbon chain of the isomerized alpha olefin (IAO) which is referred to as branching. The branching content of IAO's is monitored by infrared spectrometry (Example 2). The degree of olefin and skeletal isomerization of an NAO depends on the conditions of the isomerization process. A blend of $C_{12}$/$C_{14}$ (50:50 by weight) NAO's obtained from Chevron Phillips Chemical Company was isomerized by passing the NAO blend through a tubular fixed bed reactor (2.54 cm ID×54 cm Length Stainless Steel) packed sequentially from the bottom of the reactor to the top of the reactor as follows; 145 grams Alundum 24, 40 grams of ICR 505 mixed with 85 grams of Alundum 100, 134 grams of Alundum 24. The reactor was mounted vertically in a temperature controlled electric furnace. The catalyst was dried at approximately 150° C. in a downflow of dry nitrogen of approximately 30 ml/minute. The NAO blend was pumped upflow at a WHSV of between 0.42-0.60 while the catalyst bed was held at temperatures ranging between 140° C. and 168° C. at atmospheric pressure and samples of IAO were collected at the outlet of the reactor with different amounts of branching depending on the reactor temperature. Those samples with approximately 65% Branching were combined to provide a $C_{12}$/$C_{14}$ IAO with 65.3% Branching and 0.6% residual alpha-olefin and a BI=26.1, BP=9.4 and FCI=2.1.

EXAMPLE 2

Measurement of % Branching and % Alpha-Olefin in Isomerized Alpha Olefins

Infrared spectrometry can be used to determine the percentage of methyl branching and percentage of residual alpha-olefin of isomerized NAO's or isomerized alpha olefin (IAO). The technique involves developing a calibration curve between the infrared absorption at 1378 cm-1 (characteristic of the methyl stretch) measured by attenuated reflectance (ATR) infrared spectrometry and the percent branching determined by GLPC analysis of the corresponding hydrogenated IAO samples (hydrogenation converts the IAO to a mixture of paraffin's in which the normal paraffin has the longest retention time for a given carbon number). Similarly, a calibration curve was developed between the infrared absorption at 907 cm-1 (characteristic of alpha olefin C—H stretch) determined by attenuated reflectance (ATR) infrared spectrometry and the percent alpha-olefin determined by quantitative carbon NMR. Such a calibration curve was developed for $C_{20-24}$ IAO's and is generally applied to all carbon number IAO's realizing that since the carbon number of the IAO's may not be $C_{20-24}$, the method provides at least a measurement of the degree of branching.

The linear least squares fit of the data for the percent branching of a $C_{20-24}$ IAO showed the following equation:

% Branching by Hydrogenation GC=3.0658 (Peak Height at 1378 cm-1, in mm, by ATR Infrared Spectroscopy)−54.679.

The R2 was 0.9321 and the branching content of the samples used to generate this calibration equation ranged from approximately 9% to 92%.

Similarly, a linear least squares fit of the percent alpha-olefin data for a series of $C_{20-24}$ IAO' showed the following equation:

% Alpha-Olefin by Carbon NMR=0.5082 (Peak Height at 909 cm−1, in mm, by ATR Infrared Spectroscopy)−2.371.

The R2 was 0.9884 and the alpha-olefin content of the samples used to generate this calibration equation ranged from approximately 1% to 75%.

EXAMPLE 2B

Measurement Branching Index (BI), Branching Proximity (BP) and Free Carbon Index (FCI) of Olefins The branching properties of the olefin samples were further defined using hydrogen-1 (1H) NMR and carbon-13 (13C) NMR according to the following procedure following literature procedures. The NMR spectra were obtained using a Bruker 500 MHz NMR on 25-50 percent by weight solutions of olefin samples in chloroform-d1. The solutions were excited by 30 degrees pulses followed by a 1.3 sec acquisition time. In order to minimize non-uniform intensity data, the broadband proton inverse-gated decoupling was used during a 6 sec delay prior to the excitation pulse and on during acquisition. Samples were also doped with 0.03 to 0.05 M Cr(acac)3 (tris (acetylacetonato)-chromium(III)) as a relaxation agent to ensure full intensities are observed. Total experiment times ranged from 4 to 8 hours. The 1H NMR analysis were carried out by using the acquired free induction decay of 64 coaveraged transients employing a 90o excitation pulse, a relaxation decay of 4 seconds, and acquisition time of 1.2 seconds.

The DEPT and APT sequences were carried out according to literature descriptions with minor deviations described in the Bruker operating manuals. DEPT is Distortionless Enhancement by Polarization Transfer. The DEPT 45 sequence gives a signal all carbons bonded to protons. DEPT 90 shows CH carbons only. DEPT 135 shows CH and $CH_3$ up and $CH_2$ 180 degrees out of phase (down). APT is Attached Proton Test. It allows all carbons to be seen, but if CH and $CH_3$ are up, then quaternaries and $CH_2$ are down. The sequences are useful in that every branch methyl should have a corresponding CH. And the methyl groups are clearly identified by chemical shift and phase. Both are described in the references cited.

1) Identify the CH branch centers and the CH3 branch termination points using the DEPT Pulse sequence (Doddrell, D. T.; D. T. Pegg; M. R. Bendall, Journal of Magnetic Resonance 1982, 48, 323ff.).
2) Assign the various branch carbon resonances to specific branch positions and lengths using tabulated and calculated values (Lindeman, L. P., Journal of Qualitative Analytical Chemistry 43, 1971 1245ff; Netzel, D. A., et. al., Fuel, 60, 1981, 307ff).

EXAMPLES

| Branch | NMR Chemical Shift (ppm) |
| --- | --- |
| 2-methyl | 22.7 |
| 3-methyl | 19.3 or 11.4 |
| 4-methyl | 14.3 |
| 4 + methyl | 19.8 |
| Internal ethyl | 10.8 |
| Internal propyl | 14.5 or 20.5 |
| Adjacent methyls | 16.5 |

4) Estimate relative branching density at different carbon positions by comparing the integrated intensity of the specific carbon of the methyl/alkyl group to the intensity of a single carbon (which is equal to total integral/number of carbons per molecule in the mixture). For the unique case of the 2-methyl branch, where both the terminal and the branch methyl occur at the same resonance position, the intensity was divided by two before estimating the branching density. If the 4-methyl branch fraction is calculated and tabulated, its contribution to the 4+methyls must be subtracted to avoid double counting.

5) Estimate Branching Index (BI). The BI is estimated by 1H NMR Analysis and presented as percentage of methyl hydrogen (chemical shift range 0.6-1.05 ppm) among total hydrogen as estimated by NMR of the sample. Methyl hydrogen on olefin carbons are not considered in this calculation.

6) Estimate Branching proximity (BP). The BP is estimated by 13C NMR and presented as percentage of recurring methylene carbons which are four or more carbons away from the end group or a branch (represented by a NMR signal at 29.9 ppm) among total carbons as estimated by NMR of the sample.

7) Estimate Free Carbon Index (FCI). The FCI is presented as total number of recurring methylene carbons which are four or more carbons away from the end group or a branch or five or more carbons away from olefin carbon (represented by a NMR signal at 29.9 ppm) as estimated by 13C NMR of the sample.

The molecular interpretation of the Branching Index (BI), Branching Proximity (BP) and Free Carbon Index (FCI) can be illustrated by the following diagram:

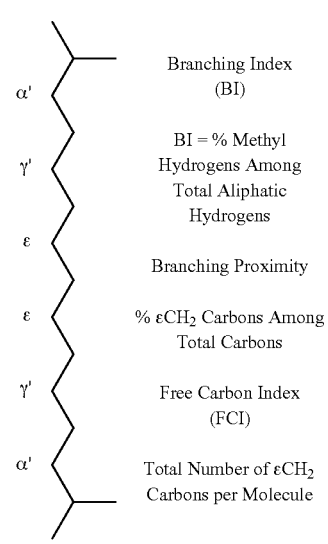 [SMILES: CC(C)CCCCCCCCCCCC(C)C]

EXAMPLE 3

Sulfonation of 65% Branched $C_{12}/C_{14}$ IAO

The 65% Branched $C_{12}/C_{14}$ IAO prepared in Example 1 was sulfonated in a glass, water jacketed, falling film tubular reactor (0.6 cm ID and three reactors in series, R1=30 cm, R2=30 cm and R3=70 cm) using $SO_3$/Air and the following conditions:
IAO Feed Temperature=50° C.
Reactor Temperature=30° C.
Air Flow=192 liters/hr
$SO_2$ Flow=16 liters/hr
$SO_2$ to $SO_3$ conversion=87%
IAO Feed Rate=1.89 grams/minute.

The crude isomerized olefin sulfonic acid produced had the following properties: 52.7 wt. % $SO_3H$ and 1.93 wt. % $H_2SO_4$ by cyclohexylamine titration.

EXAMPLE 4

Neutralization of 65% Branched $C_{12}/C_{14}$ IAO Sulfonic Acid

The IAO sulfonic acid (147.1 grams) produced in Example 3 was neutralized immediately after being produced by the addition of approximately 27.1 of 50 wt % aqueous NaOH in successive aliquouts (typically between 1 and 3 grams each) to the IAO sulfonic acid over approximately 45 minutes to 80 minutes at between 25 and 40° C. with mechanical stirring (approximately 340 rpm). The resulting neutralized sodium alpha olefin sulfonate had a pH of 10.8 (1 wt. % sample in water).

EXAMPLE 5

Hydrolysis of 65% Branched $C_{12}/C_{14}$ Neutralized Sodium IAO Sulfonate

The 65% Branched $C_{12}/C_{14}$ neutralized sodium IAO sulfonate from Example 4 (35.5 grams) was weighed into a 50 ml mechanically stirred pressure reactor (Parr Model 4590 Micro Bench Top Reactor equipped with a Parr Model 4843 temperature controller) followed by 2.2 grams of 50 wt. % aqueous NaOH solution. The reactor was sealed and heated to 140° C. with mechanical stirring (approximately 200 rpm) and held at 140° C. for 45 minutes. The reactor was then cooled to room temperature and the final sodium isomerized alpha olefin sulfonate (IOS) obtained had the following properties: pH=9.45 (1.0 wt. % aqueous solution), Activity (Hyamine Titration), Hydroxy Sulfonate (ElectroSpray Mass Spectrometry)=62.4%.

EXAMPLE 6

Preparation of 25% Branched $C_{16}/C_{18}$ Isomerized Normal Alpha Olefin

A sample of 25% Branched $C_{16-18}$ IAO was obtained from Chevron Philips Company and had the following properties: 25% Branching, 0.6% residual alpha-olefin and a BI=17.0, BP=33.0 and FCI=7.3.

EXAMPLE 7

Sulfonation of 25% Branched $C_{16}/_{18}$ IAO

The $C_{16}/C_{18}$ IAO from Example 6 was sulfonated as in Example 3 to produce an isomerized olefin sulfonic acid with the following properties: 8.2 wt. % $SO_3H$ and 1.18 wt. % $H_2SO_4$ by cyclohexylamine titration.

EXAMPLE 8

Neutralization of 25% Branched $C_{16}/_{18}$ IAO Sulfonic Acid

The IAO sulfonic acid (147.1 grams) produced in Example 7 was neutralized immediately after being produced as in Example 4 using 32.3 grams of 50 wt % aqueous NaOH. The temperature of the reaction mixture during neutralization ranged between 32 and 68° C. to afford a product with a pH=10.6 (1 wt. % sample in water).

EXAMPLE 9

Hydrolysis of 25% Branched $C_{16}/_{18}$ Neutralized Sodium IAO Sulfonate

The 25% Branched $C_{16}/_{18}$ neutralized sodium IAO sulfonate (15.0 grams) from Example 8 was hydrolyzed following the procedure of Example 5 using 4.0 grams of 50 wt % aqueous sodium hydroxide to afford the final sodium isomerized alpha olefin sulfonate (IOS) with the following properties: pH=11.6 (1.0 wt % aqueous solution), Activity 55.0% (Hyamine Titration), Hydroxy Sulfonate (ElectroSpray Mass Spectrometry)=34.9%.

EXAMPLE 10

Preparation of 65% Branched $C_{16}/_{18}$ Isomerized Normal Alpha Olefin

The 65% Branched $C_{16}/_{18}$ Isomerized Alpha Olefin (IAO) was prepared as in Example 1 using a blend of C16/C18 (50:50 by weight) NAO's obtained from Chevron Phillips Chemical Company. A WHSV between 0.59-0.63 at a catalyst bed temperature range between 168 and 182° C. was utilized. The resulting $C_{16}/_{18}$ IAO had the following properties: 64.6% Branching, 0.5% residual alpha-olefin and a BI=23.4, BP=12.9 and FCI=2.8.

EXAMPLE 11

Sulfonation of 65% Branched $C_{16}/_{18}$ IAO

The $C_{16}/_{18}$ IAO from Example 9 was sulfonated as in Example 3 to produce an isomerized olefin sulfonic acid with the following properties: 14.97 wt. % $SO_3H$ and 2.21 wt. % $H_2SO_4$ by cyclohexylamine titration

EXAMPLE 12

Neutralization of 65% Branched $C_{16}/_{18}$ IAO Sulfonic Acid

The IAO sulfonic acid (138.0 grams) produced in Example 10 was neutralized immediately after being produced as in Example 4 using 29.78 grams of 50 wt % aqueous NaOH. The temperature of the reaction mixture during neutralization ranged between 27 and 76° C. to afford a product with a pH=10.7 (1 wt. % sample in water).

EXAMPLE 13

Hydrolysis of 25% Branched $C_{16}/_{18}$ Neutralized Sodium IAO Sulfonate

The 65% Branched $C_{16}/_{18}$ neutralized sodium IAO sulfonate from Example 11 was hydrolyzed in five different batches (30.0 grams, 30.0 grams, 30.0 grams, 30.0 grams and 20.0 grams) following the procedure of Example 5 using 50 wt % aqueous sodium hydroxide (3.0, 3.0, 3.0, 3.0 and 2.0 grams) at about 140° C. for 45 minutes. The combined hydrolyzed sodium isomerized alpha olefin sulfonates (IOS's) had the following properties: pH=11.0 (1.0 wt % aqueous solution), Activity=66.6% (Hyamine Titration), Hydroxy Sulfonate (ElectroSpray Mass Spectrometry)=19.9%.

What is claimed is:

1. A method of making a skeletal isomerized alpha olefin sulfonate comprising the steps of
   (a) sulfonating an isomerized alpha olefin with sulfur trioxide in the presence of air thereby producing primarily an isomerized alpha olefin sulfonic acid, wherein the skeletal isomerized alpha olefin is derived from the skeletal isomerization of $C_{10}$-$C_{20}$ normal alpha olefins and has a Branching Index (BI) from about 10 to about 30, a Branching Proximity (BP) from about 5 to about 36 and a Free Carbon Index (FCI) from about 1 to about 10;
   (b) optionally thermally digesting the product from step (a);
   (c) neutralizing the product from step (b) with a source of an alkali metal or ammonium or substituted ammonium ion; and
   (d) optionally, hydrolyzing the product from step (c) with additional base or caustic.

2. The method of claim 1 wherein the skeletal isomerized alpha olefin has a Branching Index (BI) from about 16 to about 27, a Branching Proximity (BP) from about 9 to about 34 and a Free Carbon Index (FCI) from about 2 to about 8.

3. The method of claim 1 wherein the skeletal isomerization process is carried out in a liquid phase at atmospheric pressure.

4. The method of claim 1, wherein the product from step (a) is thermally digested by heating.

5. The method of claim 1, wherein the product from step (c) is hydrolyzed.

* * * * *